US011333623B2

(12) United States Patent
Yanagi

(10) Patent No.: US 11,333,623 B2
(45) Date of Patent: May 17, 2022

(54) HOLE FORMING METHOD AND HOLE FORMING APPARATUS

(71) Applicant: HITACHI HIGH-TECH CORPORATION, Tokyo (JP)

(72) Inventor: Itaru Yanagi, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 127 days.

(21) Appl. No.: 16/769,118

(22) PCT Filed: Nov. 9, 2018

(86) PCT No.: PCT/JP2018/041694
§ 371 (c)(1),
(2) Date: Jun. 2, 2020

(87) PCT Pub. No.: WO2019/111634
PCT Pub. Date: Jun. 13, 2019

(65) Prior Publication Data
US 2021/0223194 A1 Jul. 22, 2021

(30) Foreign Application Priority Data

Dec. 5, 2017 (JP) .............................. JP2017-233344

(51) Int. Cl.
H01L 21/3063 (2006.01)
G01N 27/00 (2006.01)

(52) U.S. Cl.
CPC ....... G01N 27/002 (2013.01); H01L 21/3063 (2013.01)

(58) Field of Classification Search
CPC ............. H01L 21/3063; G01N 27/002; G01N 33/48721
See application file for complete search history.

(56) References Cited

U.S. PATENT DOCUMENTS

2014/0063866 A1 3/2014 Wang et al.
2014/0262820 A1 9/2014 Kuan et al.
(Continued)

FOREIGN PATENT DOCUMENTS

JP 2015-197385 A 11/2015
WO 2013-167955 A1 11/2013
(Continued)

OTHER PUBLICATIONS

Rosenstein, J., et al., "Integrated nanopore sensing platform with sub-microsecond temporal resolution," vol. 9, No. 5, pp. 487-492 (2012); vol. 6, No. 4, pp. 779-782.
(Continued)

Primary Examiner — Binh X Tran
(74) Attorney, Agent, or Firm — Volpe Koenig

(57) ABSTRACT

Provided are a hole forming method and a hole forming apparatus capable of stably forming a single nanopore on a membrane. This hole forming method is a hole forming method for forming a hole in a film and includes: a first step of applying a first voltage between a first electrode and a second electrode, installed so as to sandwich the film provided in an electrolyte, and stopping the application of the first voltage when a current flowing between the first electrode and the second electrode reaches a first threshold current so as to form a thin film portion in a part of the film; and a second step of applying a second voltage between the first electrode and the second electrode after the first step so as to form a nanopore in the thin film portion.

23 Claims, 13 Drawing Sheets

(56) References Cited

U.S. PATENT DOCUMENTS

2015/0109008 A1     4/2015   Godin et al.
2016/0327513 A1*   11/2016   Yanagi ............. G01N 27/44713
2017/0138899 A1*   5/2017   Itabashi ............... G01N 21/658
2018/0080072 A1*   3/2018   Li .................... G01N 33/48721

FOREIGN PATENT DOCUMENTS

WO       2015-097765 A1    7/2015
WO    WO-2015152003 A1 * 10/2015     ....... G01N 33/48721

OTHER PUBLICATIONS

Yanagi et al., Fabricating nanopores with diameters of sub-1 nm to 3 nm using multilevel pulse-voltage injection, Scientific Reports, vol. 4, dated May 21, 2014.

Yanagi et al., Two-step breakdown of a SiN membrane for nanopore fabrication: Formation of thin portion and penetration, Scientific Reports, vol. 8, No. 1, dated Jul. 4, 2018.

Extended European Search Report dated Jul. 15, 2021 for European Patent Application No. 18886281.7.

* cited by examiner

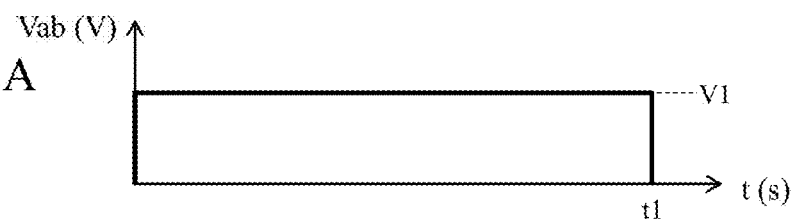
FIG. 2A
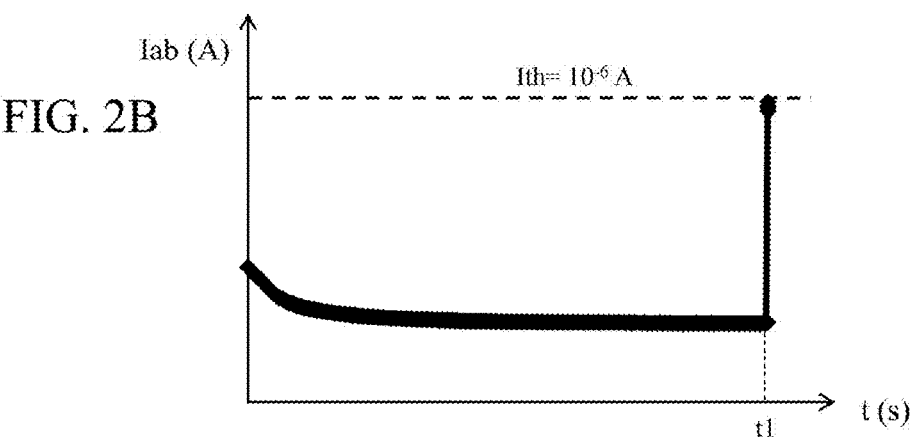
FIG. 2B
FIG. 3
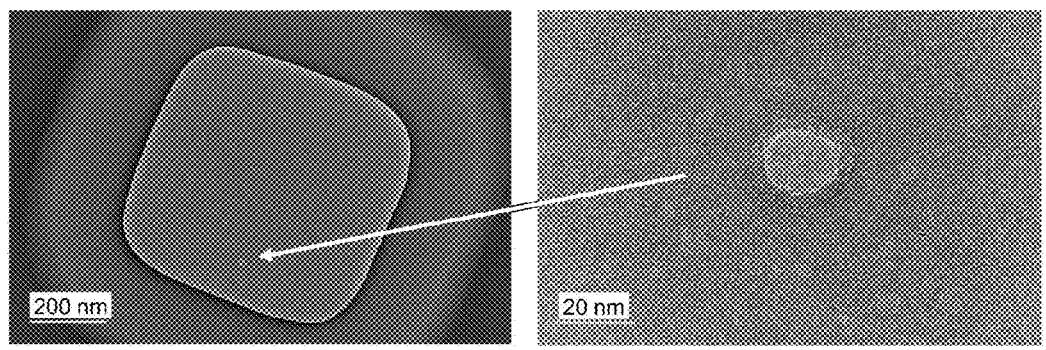
$Ith = 10^{-6} A$ $Ith = 2 \times 10^{-6} A$

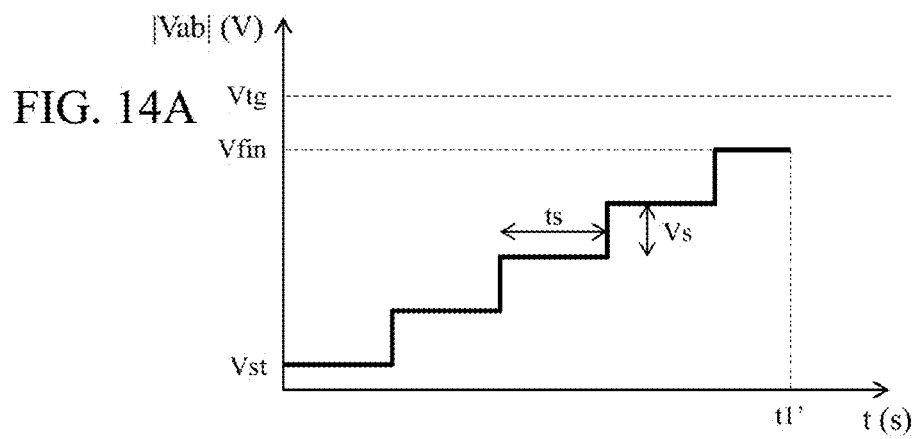
FIG. 14A
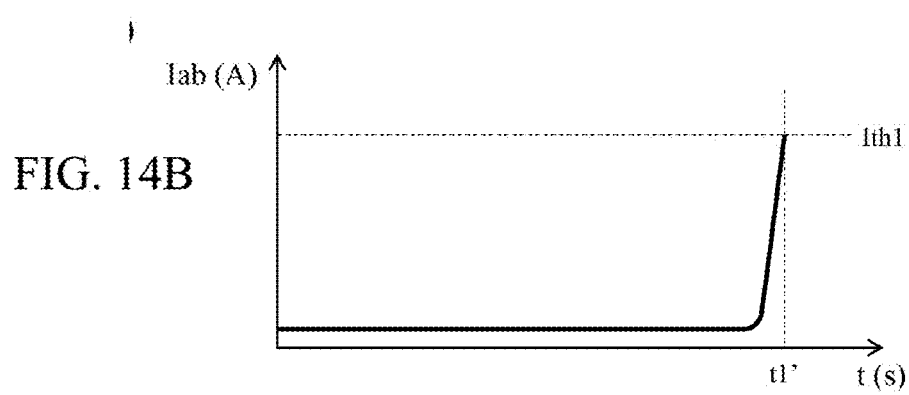
FIG. 14B
FIG. 15
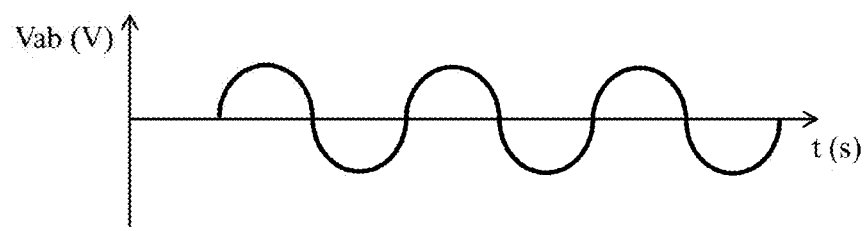

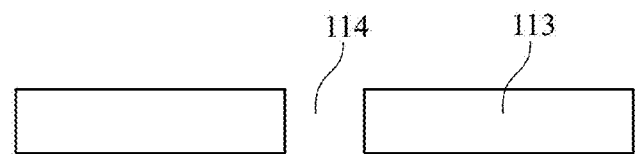
FIG. 19A
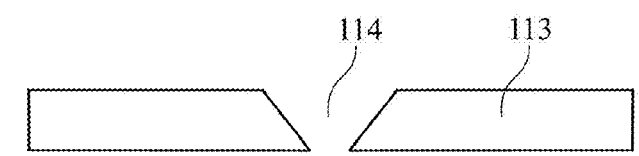
FIG. 19B
FIG.20
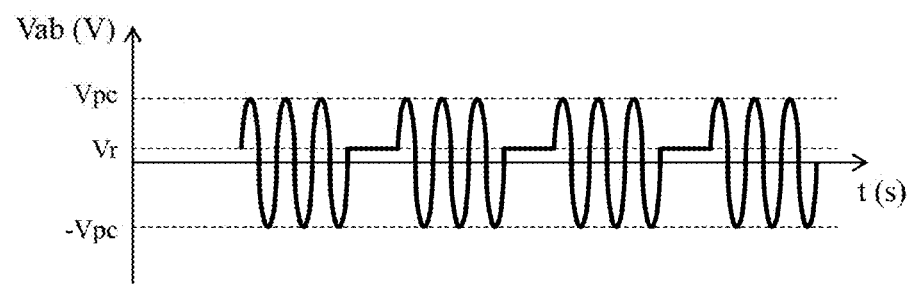
FIG.21
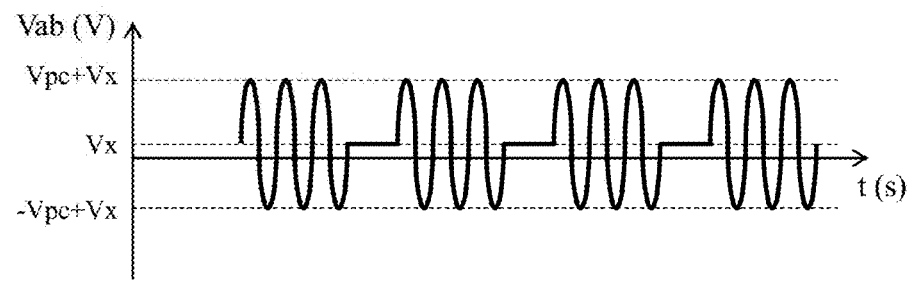

HOLE FORMING METHOD AND HOLE FORMING APPARATUS

TECHNICAL FIELD

The present invention relates to a hole forming method and a hole forming apparatus.

BACKGROUND ART

Research and development on a technique using nanopores (through-holes on the order of nanometers) have progressed as means for detecting molecules and particles present in an electrolyte. In this technique, a hole (nanopore) of the same size as a molecule or a particle to be detected is formed on a membrane (film). Then, upper and lower chambers of the membrane are filled with the electrolyte, and both the upper and lower chambers are provided with electrodes that are in contact with the electrolyte. A detection target to be measured is placed on one side of the chamber, a potential difference is given between the electrodes provided in both the chambers so that the detection target is electrophoresed to pass through the nanopore. In so doing, a temporal change of an ion current flowing between both the electrodes is measured. As a result, it is possible to detect the passage of the detection target and to grasp its structural characteristics. A device having a membrane or the like in which such a nanopore has been formed is generally called a nanopore device.

Regarding the manufacture of nanopore devices, a method using a semiconductor substrate, a semiconductor material, and a semiconductor process has attracted attention because of its high mechanical strength and the like. For example, a silicon nitride film (SiN film) can be used as a material of the membrane, and a transmission electron microscope (TEM) can be used as a device for the nanopore formation. In the TEM, a nanopore having a diameter of 10 nm or less can be formed by narrowing an irradiation area of an electron beam on a membrane and controlling energy or current (NPL 1).

PTL 1 discloses a new method for forming nanopores using a dielectric breakdown phenomenon of a membrane. In the method of PTL 1, first, a membrane having no hole therein is filled with an electrolyte to be sandwiched by the electrolyte at the upper and lower side thereof, and electrodes are immersed in the electrolyte in upper and lower chambers, and a high voltage is continuously applied between both the electrodes. Then, when a current value between the electrodes sharply rises and reaches a predetermined threshold current, it is determined that a nanopore has been formed, and the application of the high voltage is stopped. The method of PTL 1 has an advantage that manufacturing cost and throughput are significantly reduced as compared with the nanopore formation using the TEM device. After forming the nanopore in the film, it is possible to proceed to measurement of a detection target without removing the membrane from the chamber. Therefore, there is an advantage that the nanopore is not exposed to pollutants in the atmosphere, and noise during the measurement is reduced.

However, as a result of tests conducted by the present inventors, it has been found that it is difficult to stably form a nanopore with the method of PTL 1. Specifically, it has been found that, when formation of the nanopore by dielectric breakdown is tried on a membrane having a thickness larger than 5 nm, it is almost impossible to form a single nanopore in the membrane with the method of PTL 1, although it is possible to form a nanopore that is effective to a certain extent on a membrane having a thickness of 5 nm or less (in other words, in some cases, a single nanopore can be formed, whereas in other cases it cannot be formed in the film).

CITATION LIST

Non-Patent Literature

NPL 1: Jacob K Rosenstein, et al., Nature Methods, Vol. 9, No. 5, 487 to 492 (2012) Vol. 6, No. 4, 779 to 782

Patent Literature

PTL 1: WO 2013/167955 A

SUMMARY OF INVENTION

Technical Problem

The present invention provides a hole forming method and a hole forming apparatus capable of stably forming a single nanopore on a membrane.

Solution to Problem

A hole forming method according to the present invention is a hole forming method for forming a hole on a membrane, and includes: a first step of applying a first voltage between a first electrode and a second electrode, installed so as to sandwich the film provided in an electrolyte, and stopping the application of the first voltage when a current flowing between the first electrode and the second electrode reaches a first threshold current so as to form a thin film portion in a part of the film; and a second step of applying a second voltage between the first electrode and the second electrode after the first step so as to form a nanopore in the thin film portion.

In addition, a hole forming apparatus according to the present invention includes: a first electrode and a second electrode arranged so as to sandwich a film provided in an electrolyte; and a control unit that applies a voltage to the first electrode and the second electrode and measures a current flowing between the first electrode and the second electrode. The control unit is configured to be capable of executing: a first step of applying a first voltage between the first electrode and the second electrode and stopping the application of the first voltage when the current flowing between the first electrode and the second electrode reaches a first threshold current so as to form a thin film portion in a part of the film; and a second step of applying a second voltage between the first electrode and the second electrode after the first step so as to form a nanopore in the thin film portion.

Advantageous Effects of Invention

According to the present invention, the hole forming method and the hole forming apparatus capable of stably forming the single nanopore in the membrane are provided.

BRIEF DESCRIPTION OF DRAWINGS

FIGS. 2A and 2B are a graph for describing a procedure of nanopore formation according to PTL 1.

FIG. 3 is an image illustrating a result of nanopore formation according to PTL 1.

FIGS. 14A and 14B are a graph for describing a hole forming method according to a third embodiment.

FIG. 15 is a graph for describing a hole forming method according to a fourth embodiment.

FIGS. 19A and 19B are a conceptual diagram for describing an effect of the hole forming method according to the fourth embodiment.

FIG. 20 is a graph for describing a hole forming method according to a fifth embodiment.

FIG. 21 is a graph for describing the hole forming method according to the fifth embodiment.

DESCRIPTION OF EMBODIMENTS

Figure 1:
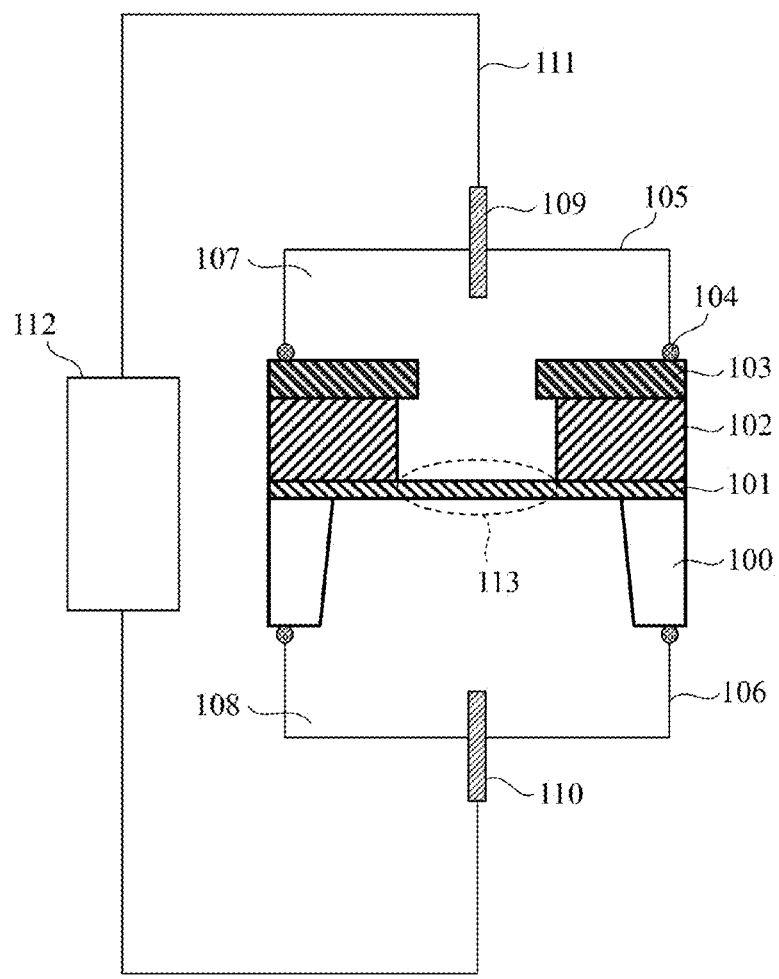
FIG. 1 is a schematic view illustrating a hole forming apparatus according to a first embodiment.

Hereinafter, embodiments of the present invention will be described in detail with reference to the drawings. The same reference numerals will be attached to those having the same function in the entire drawing for describing the embodiments, and the repetitive description thereof will be omitted as much as possible. Device structures and materials described in the embodiments are examples for embodying the idea of the present invention, and do not strictly specify materials and dimensions, and are not disclosed in order to limit the scope of the present invention. In addition, it should be noted that specific voltage value, current value, voltage application time, voltage pulse time width described in the embodiments are also examples for embodying the idea of the present invention, do not strictly specify them, and are not disclosed with the intention of limiting the scope.

First Embodiment

First, a hole forming apparatus and a hole forming method according to a first embodiment will be described with reference to the drawings. FIG. 1 is a schematic view illustrating the hole forming apparatus according to the first embodiment. A processing target of the hole forming apparatus according to the first embodiment is, for example, a film including a Si substrate 100, a silicon nitride film (SiN film) 101 formed on the Si substrate 100, a silicon oxide film ($SiO_2$ film) 102 formed on the SiN film 101, and a silicon nitride film (SiN film) 103 formed on the $SiO_2$ film 102. A portion of the silicon nitride film 101 of this film where the $SiO_2$ film 102 or the Si substrate 100 does not exist above and below (the portion surrounded by the dotted line in FIG. 1) is a membrane 113 described above, and is a target on which a hole (nanopore) is to be formed.

For example, the silicon oxide film ($SiO_2$ film) 102 has a thickness of about 250 nm, and the silicon nitride film (SiN film) 103 has a thickness of about 100 nm.

The hole forming apparatus includes an O-ring 104 and chambers 105 and 106. The chambers 105 and 106 are configured so that the inside thereof may be filled with electrolytes 107 and 108. In addition, electrodes 109 and 110 are arranged in the chambers 105 and 106 so as to be in contact with electrolytes 107 and 108. Note that the electrolytes 107 and 108 are, for example, potassium chloride (KCl) aqueous solutions. In addition, the electrodes 109 and 110 are, for example, Ag/AgCl electrodes. These electrodes 109 and 110 are connected to a measurement control unit 112 by an electric wire 111.

The measurement control unit 112 is configured to be capable of applying voltages of various values between the electrodes 109 and 110 and measuring a current flowing between the electrodes 109 and 110. In addition, the measurement control unit 112 can also perform control to automatically stop the voltage application between the electrode 109 and the electrode 110 when a value of the current flowing between the electrode 109 and the electrode 110 reaches a certain threshold current.

In this hole forming apparatus, a nanopore is formed in the membrane 113 by executing two steps of a first step and a second step as will be described later. In the first step, a voltage V1 is applied between the electrode 109 and the electrode 110 installed so as to sandwich the membrane 113 provided in the electrolytes 107 and 108, the application of the voltage V1 is stopped when the current flowing between the electrode 109 and the electrode 110 (through the electrolytes 107 and 108 and the silicon nitride film 103) reaches the threshold current, thereby forming a thin film portion in a part of the membrane 113. A thickness of the thin film portion is smaller than a thickness of the original membrane 113. In the next second step, a nanopore is formed to penetrate this thin film portion.

Meanwhile, in the second step, a voltage V2 is applied between the electrode 109 and the electrode 110 after the first step so as to form a nanopore in the thin film portion. Since such two-stage processing including the first step and the second step is performed, the single nanopore can be stably formed in the membrane. The voltage V2 has an absolute value smaller than that of the voltage V1. A specific voltage application method will be described later. Specific control is executed by the above-described measurement control unit 112.

Note that the measurement control unit 112 can also include a storage unit (not illustrated) that stores specific parameter values necessary to perform the first step and the second step (values and types of the voltage, a value of the threshold current configured to end the first and second steps, and the like). Such parameters are stored in advance for membranes formed with various thicknesses and materials, respectively. In addition, parameters corresponding to a size and a shape of a nanopore to be formed, can be also stored. A user using this hole forming apparatus can form a hole (nanopore) of a desired size on membranes of various thicknesses and materials by performing the first step and the second step using such information in the storage unit.

Here, a hole forming method disclosed in PTL 1 is the same as the first embodiment (FIG. 1) in terms of an appearance of an apparatus that executes the method, but is different from the first embodiment in terms of the control performed by the measurement control unit 112. That is, in the hole forming method disclosed in PTL 1, voltage application is not performed in two stages (a first step and a second step) as in the first embodiment, and the voltage application is performed in only one step. A procedure of nanopore formation according to PTL 1 and a result thereof will be described with reference to FIGS. 2A and 2B to 7.

In the method of PTL 1, a current Iab flowing between the electrode 109 and the electrode 110 is measured while a voltage Vab=V1 (constant value) is applied between the electrode 109 and the electrode 110 as illustrated in FIG. 2A. The current Iab between the electrodes 109 to 110 sharply increases, for example, around time t1, it is determined that a nanopore has been formed when a predetermined threshold current Ith is reached, and at the point of time, the voltage application between the electrodes 109 and 110 is stopped. As a result, the nanopore is formed in the membrane 113.

It has been found by experiments of the inventors that it is impossible or extremely difficult to form a single nanopore in the membrane 113 when the method of PTL 1 is used, particularly when a thickness of the membrane 113 is 5 nm or more.

An experimental example in which nanopore formation was attempted using the method of PTL 1 is described as follows. A thickness of the membrane 113 in this experimental example is 20 nm. A graph of FIG. 2B illustrates a temporal change of the current Iab flowing between the electrodes 109 and 110 at the time of applying 0 V to the electrode 109 and 20 V to the electrode 110. The measurement control unit 112 was set so as to automatically stop the application of the voltage between the electrodes 109 and 110 immediately when the current Iab reached the threshold current Ith=$10^{-6}$ A. As can be found from the graph of FIG. 2B, the value of the current Iab sharply increased around the time t1, and reached the threshold current Ith (=$10^{-6}$ A), and as a result, the application of the voltage Vab was stopped.

FIG. 3 illustrates TEM images obtained by observing whether or not a nanopore has been formed in the membrane 113 after performing the above processing. An image on the left side of FIG. 3 is an image of the entire view of the membrane 113 having a thickness of 20 nm as viewed from above. The TEM image of FIG. 3 illustrates that a portion having a brighter color is a portion that is thinner in the film. In the image on the left side of FIG. 3, it can be found that the membrane 113 partially has a portion having a bright color. An enlarged image of this portion is an image on the right side of FIG. 3. When viewing the image on the right side of FIG. 3, no hole has been opened, and only a thin film region having a diameter of about 20 nm has been formed. It is found that an amorphous pattern derived from SiN is visible in the thin film region having the diameter of about 20 nm, and no hole has been formed in the thin film portion.

Next, a description will be given with reference to FIG. 4 regarding a temporal change of the current Iab in the case where 0 V is applied to the electrode 109, and 20 V is applied to the electrode 110, and the measurement control unit 112 is set so as to automatically stop the application of the voltage between the electrodes 109 and 110 immediately when the current Iab between the electrodes 109 and 110 reaches the threshold current Ith=$2\times10^{-6}$ A. Even in this experiment, a thickness of the used membrane 113 is 20 nm. The threshold current Ith is set to a value that is twice as large as that in the case of FIGS. 2A, 2B and 3.

Figure 4:
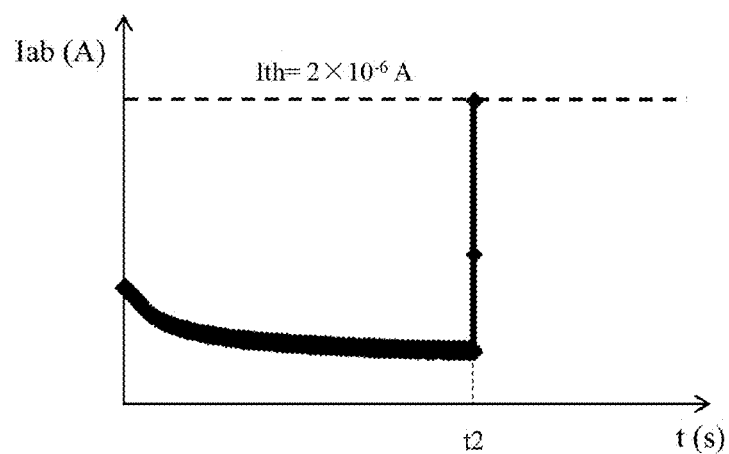
FIG. 4 is a graph for describing a procedure of nanopore formation according to PTL 1.
Figure 5:
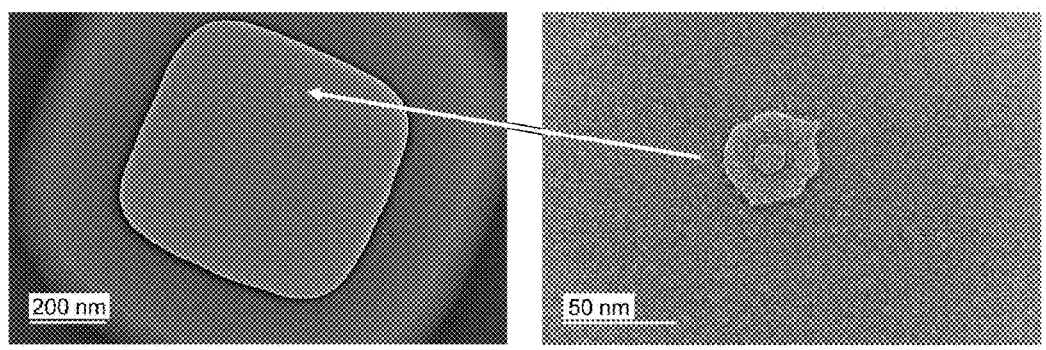
FIG. 5 is an image illustrating a result of nanopore formation according to PTL 1.

As can be found from a graph of FIG. 4, the value of the current Iab between the electrodes 109 and 110 sharply increases around time t=t2, and reaches the predetermined threshold current Ith (=$2\times10^{-6}$ A). FIG. 5 illustrates TEM images obtained by observing whether or not a nanopore has been formed in the membrane 113 after performing the above processing. An image on the left side of FIG. 5 is an image of the entire view of the membrane 113 having a thickness of 20 nm as viewed from above. In the image on the left side of FIG. 5, it can be found that the membrane 113 partially has a portion having a bright color. An enlarged image of this portion is an image on the right side of FIG. 5. When viewing the image on the right side of FIG. 5, it can be found that a larger thin film region has been formed than that in the case of FIG. 3, but it can be also understood that no hole has been formed.

Next, a description will be given with reference to FIG. 6 regarding a temporal change of the current Iab in the case where 0 V is applied to the electrode 109, and 20 V is applied to the electrode 110, and the measurement control unit 112 is set so as to automatically stop the application of the voltage between the electrodes 109 and 110 immediately when the current Iab between the electrodes 109 and 110 reaches the threshold current Ith=$1\times10^{-3}$ A. Even in this experiment, a thickness of the used membrane 113 is 20 nm. A value of the threshold current Ith is even higher than that in the case of FIG. 4, and is ten times as large as that in the case of FIGS. 2A and 2B.

Figure 6:
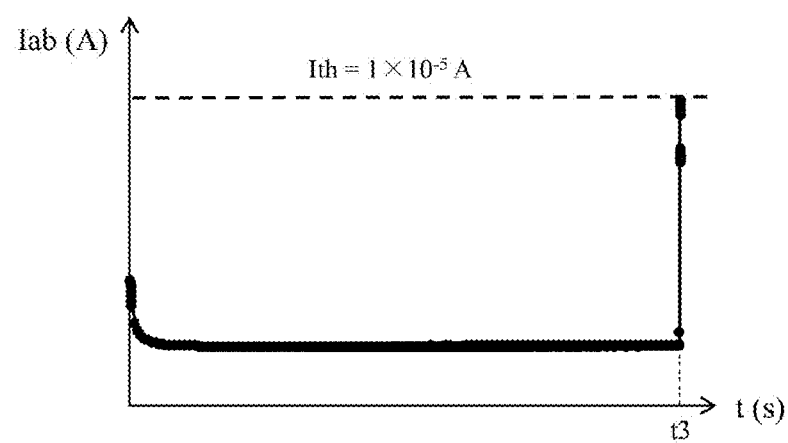
FIG. 6 is a graph for describing the procedure of nanopore formation according to PTL 1.
Figure 7:
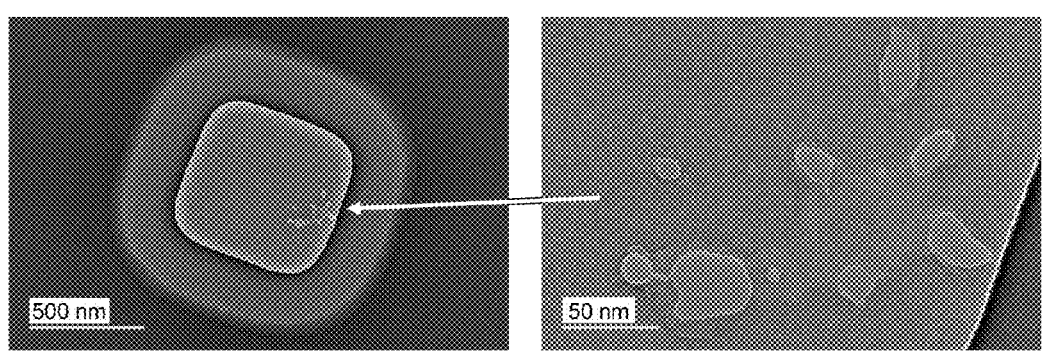
FIG. 7 is an image illustrating a result of nanopore formation according to PTL 1.

As can be found from a graph of FIG. 6, the current Iab between the electrodes 109 and 110 sharply increases around time t3, and reaches the predetermined threshold current Ith (=$1\times10^{-5}$ A). FIG. 7 illustrates TEM images obtained by observing whether or not a nanopore has been formed in the membrane 113 after performing the above processing. An image on the left side of FIG. 7 is an image of the entire view of the membrane 113 having a thickness of 20 nm as viewed from above. In the image on the left side of FIG. 7, it can be found that 113 of the membrane partially has a portion having a bright color. An enlarged image of this portion is an image on the right side of FIG. 7.

Based on the image on the right side of FIG. 7, it can be found that there is a portion where the amorphous pattern derived from SiN is not observed, and there is a portion where holes have been formed. However, a plurality of holes having different sizes have been formed in one membrane.

In detecting or counting the molecules or particles that pass through the nanopores, if the plurality of nanopores are opened in one membrane 113, the molecules or particles to be detected may enter the plurality of nanopores at the same time. In such a case, a change in ion current passing through the nanopores become complicated, and as a result, the accuracy of detecting or counting of the molecules or particles to be detected is lowered. Therefore, it is desirable that the number of nanopores present in one membrane 113 be one. In addition, another problem is that holes having various sizes are formed. This is because the molecules or particles to be detected cannot pass through holes when only the holes smaller than the molecules or particles to be detected have been formed, and as a result, it becomes impossible to detect or count the molecules or particles to be detected.

As illustrated in FIGS. 2A and 2B to 7, no hole is opened in the membrane 113 when the value of the threshold current Ith is set to be low. Conversely, when the threshold current Ith is set to be high, although the holes are opened, a plurality of holes having different sizes are formed in one membrane 113. Note that it has been found by experiments of the inventors that either no hole is opened in the membrane 113 or a plurality of holes having different sizes are formed even if the value of the threshold current Ith is set to a value between $2\times10^{-6}$ A and $1\times10^{-5}$ A. That is, it has been found that it is impossible or extremely difficult to form a single nanopore in the membrane 113 having the thickness of 20 nm with the method of PTL 1. This tendency has been confirmed even with the membrane 113 having a thickness of 20 nm or more. In addition, the above tendency has also been confirmed with the membrane 113 having a thickness of 20 nm or less.

Here, a thickness of a membrane on which a nanopore is formed will be described. The most noticeable application of measurement using the nanopore is decoding of DNA sequence (DNA sequencing). That is, the most noticeable application is a method of determining a sequence of four types of bases in a DNA strand by detecting a change in ionic current passing through nanopores when DNA passes through the nanopores. In this case, it is preferable for a membrane to have a smaller thickness. This is because an interval between the four types of bases arranged in the DNA strand is about 0.5 nm and more bases enter the nanopores at the same time as the thickness of the membrane is larger than the interval. Then, a signal obtained by current measurement also becomes a signal derived from a plurality of bases, which causes a decrease of the sequence determination accuracy and makes signal analysis more complicated.

Another application of measurement using the nanopore is in detection and counting of specific targets in an aqueous solution. For example, in Ru-Jia Yu, Yi-Lun Ying, Yong-Xu Hu, Rui Gao, and Yi-Tao Long, "Label-Free Monitoring of Single Molecule Immunoreaction with a Nanopipette" Anal. Chem. 89, 8203-8206, DOI: 10.1021/acs.analchem.7b01921 (2017), a change in ionic current is measured when an antigen, or an object in which antigen is attached to an antibody, in an aqueous solution, passes through a nanopore having a pore diameter of about 30 nm, thereby detecting and counting such targets.

In this application such as the counting of targets, it is preferable if the passage of the target can be detected as the change in ion current, and it is unnecessary to perform even the structure determination of a molecular sequence of a target molecule as in the case of performing the DNA sequencing using the nanopore. Therefore, it is unnecessary to make the thickness of the membrane as thin as possible, but rather, it is desirable that the thickness of the membrane constituting the nanopore be large to some extent when the nanopore is used for the application such as the counting of targets. This is because the mechanical strength of the membrane is improved if the membrane has the larger thickness, and the probability that the membrane is damaged decreases at the time of handling the membrane during the measurement or before the measurement, or at the time of bringing the membrane into contact with the aqueous solution.

The hole forming apparatus and the hole forming method according to the first embodiment can stably form the single nanopore in one membrane by executing the two steps of the first step and the second step as described above.

Figure 8A:
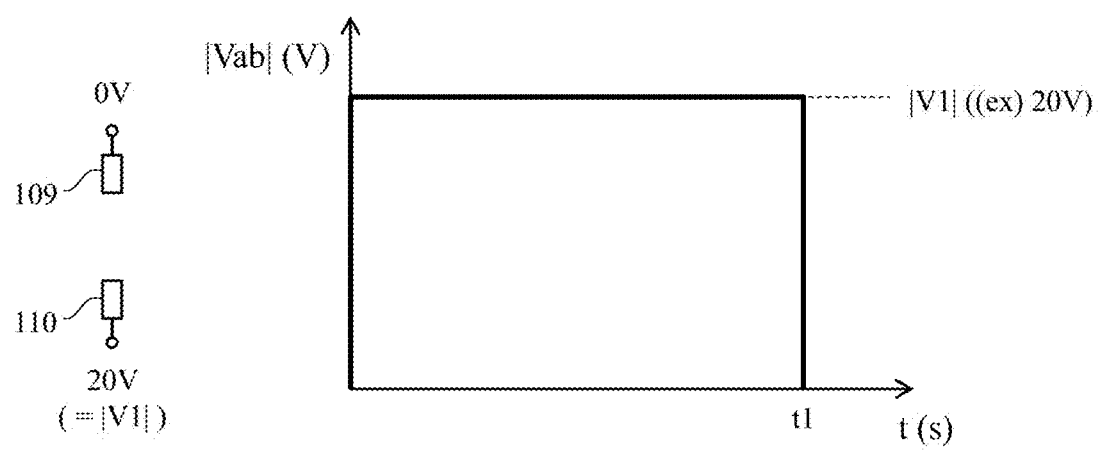
FIGS. 8A and 8B are a graph for describing the hole forming method according to the first embodiment.
Figure 8B:
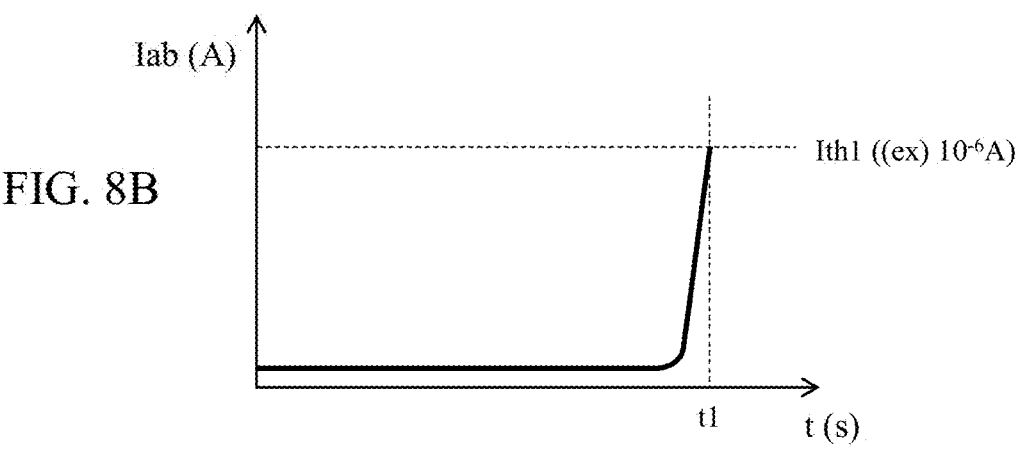
Figure 9A:
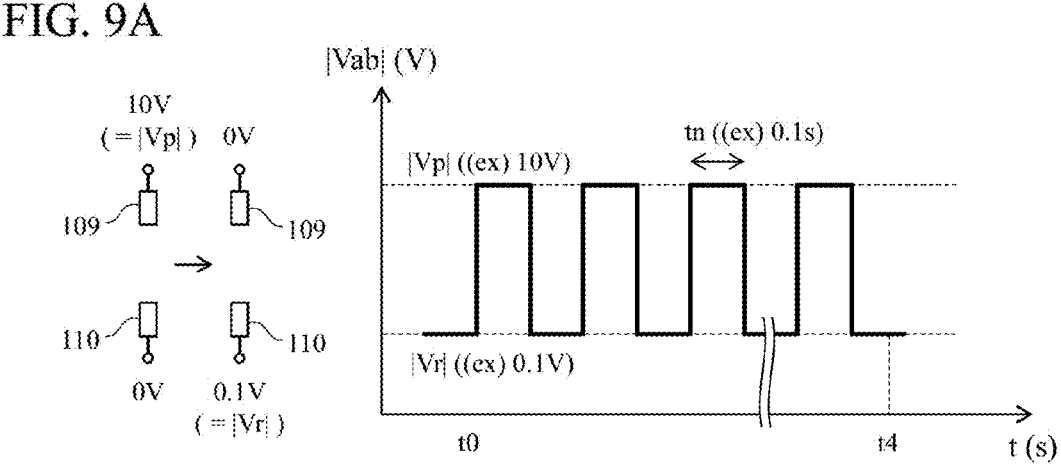
FIGS. 9A and 9B are a schematic view and a graph for describing the hole forming method according to the first embodiment.
Figure 9B:
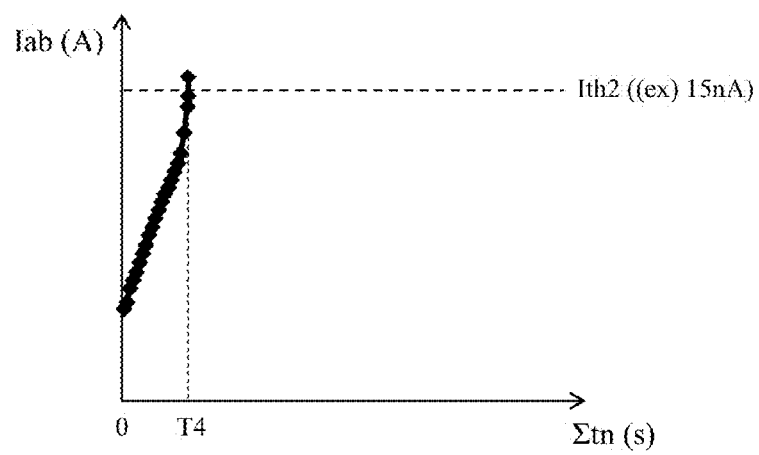

With reference to FIGS. 8A, 8B FIGS. 9A and 9B, the hole forming method using the hole forming apparatus according to the first embodiment will be described. FIGS. 8A and 8B illustrate a method for applying a voltage and detecting a current in the first step. In addition, FIGS. 9A and 9B illustrate a method for applying a voltage and detecting a current in the second step.

As illustrated in FIG. 8A, in the first step, an absolute value |Vab| of the voltage Vab applied between the electrodes 109 and 110 is set to |V1| (for example, 20 V) (here, set by applying 0 V to the electrode 109 and 20 V to the electrode 110), and the application of the voltage V1 between the electrodes 109 and 110 is stopped when the current Iab between the electrodes 109 and 110 reaches a threshold current Ith1 (for example, $10^{-6}$ A) (FIG. 8B). As a result, a thin film portion (that is not an opening) of a desired size is formed in the membrane 113.

A value of the threshold current Ith1 can be appropriately adjusted, but is set to such a value that a hole (opening) is not formed in the membrane 113 by the application of the voltage V1 and the thin film portion not penetrating through the membrane 113 is formed. For example, when a thickness of the membrane is 20 nm, the thin film portion having a diameter of about 20 to 25 nm can be formed by setting the threshold current Ith1 to $1\times10^{-6}$ A. The inventors have conducted an experiment with the same settings (that is, the same threshold current ($=1\times10^{-6}$ A)) using a plurality of membrane chips having the same dimension and the same configuration, and as a result, have confirmed that a thin film portion having a diameter of about 20 to 25 nm is formed in the membrane almost every time. In addition, it has been confirmed that a thin film portion having a diameter of about 40 m can be formed when the threshold current is set to $2\times10^{-6}$ A.

Next, the second step performed subsequently to the first step in the first embodiment will be described with reference to FIGS. 9A and 9B. FIG. 9A is a schematic view and a graph illustrating an application voltage in the second step, and FIG. 9B is a graph illustrating a change in current in the second step.

When the above-described thin film portion is formed in the membrane 113 in the first step, the second step is subsequently performed. In the second step, the absolute value Vab of the voltage Vab between the electrodes 109 and 110 is set to a voltage Vp (|Vp|<|V1|) that is smaller than the absolute value of the voltage V1 applied in the first step. With the voltage application in the second step, the thin film portion in the membrane 113 formed in the first step is broken (penetrated) to form a nanopore in the membrane 113.

As a preferred example, the voltage Vp can be applied as a pulse voltage in the second step. For example, as illustrated in FIG. 9A, it is possible to repeat the application of the pulse voltage (the voltage Vp with a pulse width tn) between the electrodes 109 and 110 and the application of a voltage Vr (|Vr|<|Vp|) whose absolute value is smaller than the absolute value of the voltage Vp during a period between the respective pulse voltages. The pulse voltage having the voltage value Vp is a voltage configured to break the above-described thin film portion. On the other hand, the voltage Vr is applied to measure the current Iab flowing between the electrodes 109 and 110 by the voltage Vr, and determine the degree of breakdown of the thin film portion. Then, as illustrated in FIG. 9B, the second step (the application of the pulse voltage) is stopped when a value of the current Iab flowing between the electrodes 109 and 110 in the case of applying the voltage of the voltage value Vr reaches or exceeds a predetermined threshold current Ith2, whereby the nanopore of a desired size can be accurately formed in the membrane 113. The horizontal axis of the graph in FIG. 9B indicates an integrated time (Σtn) of an application time of the voltage pulse. The vertical axis of the graph in FIG. 9B indicates the current Iab flowing between the electrodes 109 and 110 with Vr. A current value (Y intercept) Iint when the horizontal axis (integrated time Σtn) of the graph of FIG. 9(b) is zero is a value of the current Iab between the electrodes 109 and 110 before the pulse voltage is applied (prior to time t0 in FIGS. 9A and 9B).

Note that FIG. 9A illustrates an example in which a positive voltage (for example, 10 V) is applied to the electrode 109, and 0 V is applied to the electrode 110. Since 0 V is applied to the electrode 109 and a positive voltage (20 V) is applied to the electrode 110 in the first step as illustrated in FIGS. 8A and 8B, the application voltage V1 in the first step and the application voltage Vp in the second step have polarities or orientations opposite to each other (opposite polarities). The meaning thereof will be described later. Note that an application voltage when the degree of breakdown of the thin film portion is determined by applying the voltage Vr may have the opposite polarity of the polarity of the application voltage in the first step, or may have the same polarity. The example of FIGS. 9A and 9B illustrate a case where 0 V is applied to the electrode 109, 0.1 V is applied to the electrode 110, and the determination is performed using the voltage Vr having the same polarity as the polarity of the application voltage in the first step.

Hereinafter, illustrated are various parameter setting examples and results thereof in the case of using the membrane 113 having a thickness of 20 nm, applying 0 V to the electrode 109 and 20 V to the electrode 110 in the first step, stopping the voltage application between the electrodes 109 and 110 when the threshold current Ith1=$10^{-6}$ A is reached to form the thin film portion in the membrane, and then, performing the second step by the above-described pulse application. In this example, the pulse voltage Vp is applied by setting the electrode 109 to 10 V and the electrode 110 to 0 V, and the voltage Vr is applied by setting the electrode 109 to 0 V and the electrode 110 to 0.1 V. The pulse width tn of the pulse voltage is set to 0.1 s, and the threshold current Ith2 is set to 15 nA. In such a case, when a j-th pulse is applied at time T4, the integrated time Σtn of the voltage pulse application time reaches T4 (=j×tn), the current Iab measured at the voltage Vr becomes equal to or larger than the threshold current Ith2=15 nA, and as a result, the second step is ended, as exactly illustrated in FIG. 9B. Since the pulse width of the pulse voltage is tn=0.1 s, the respective current values are plotted in the graph at intervals of 0.1 s.

Note that these numeric values of the voltage values and pulse widths described above are merely examples. For example, the pulse width tn can be appropriately changed according to a value of the voltage Vp, a thickness and a material of the membrane 113, a size of a hole to be desirably formed, and other conditions. In addition, the pulse width tn may be constant or can be also decreased (or increased) whenever the number of times of applying the pulse voltage increases. In addition, Vp, Vr, and Ith2 can also be appropriately changed according to the thickness and material of the membrane 113, the size of the hole to be desirably formed, and other conditions.

Figure 10:
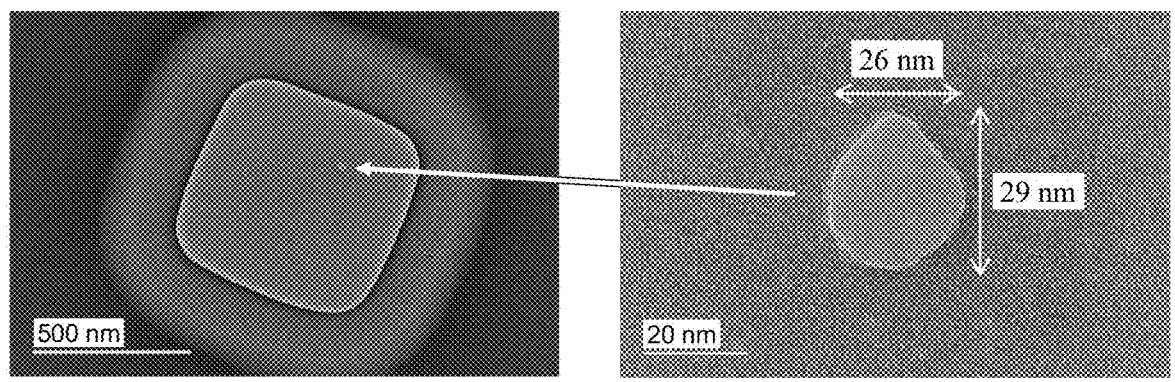
FIG. 10 is an image illustrating a result of the hole forming method according to the first embodiment.

FIG. 10 illustrates TEM images obtained by observing whether or not a nanopore has been formed in the membrane 113 after the end of the second step under the above settings. An image on the left side of FIG. 10 is an image of the entire view of the membrane 113 having a thickness of 20 nm as viewed from above. In the image on the left side of FIG. 10, it can be found that the membrane 113 partially has a portion having a bright color. An enlarged image of this portion is an image on the right side of FIG. 10. When viewing the image on the right side of FIG. 10, it has been confirmed that the amorphous pattern derived from SiN is not observed in a portion having a bright color, and a hole is opened in the bright portion.

In addition, it can be found from the image on the left side of FIG. 10 that only one hole (single nanopore) is opened in one membrane 113. Then, from the image on the right side of FIG. 10, it can be found that a long diameter of the hole is about 29 nm and a short diameter of the hole is about 26 nm. The present inventors have repeated this experiment ten times or more under the same conditions as described above using ten or more membranes having the same dimension and the same structure, and observed the resultant membranes by the TEM to observe formed holes. As a result, it has been confirmed that both long diameters and short diameters of the holes fall within the range of 20 nm to 30 nm with a probability of about 80%. In addition, it has also been confirmed that the holes are opened with a probability of 80% or more.

Figure 11A:
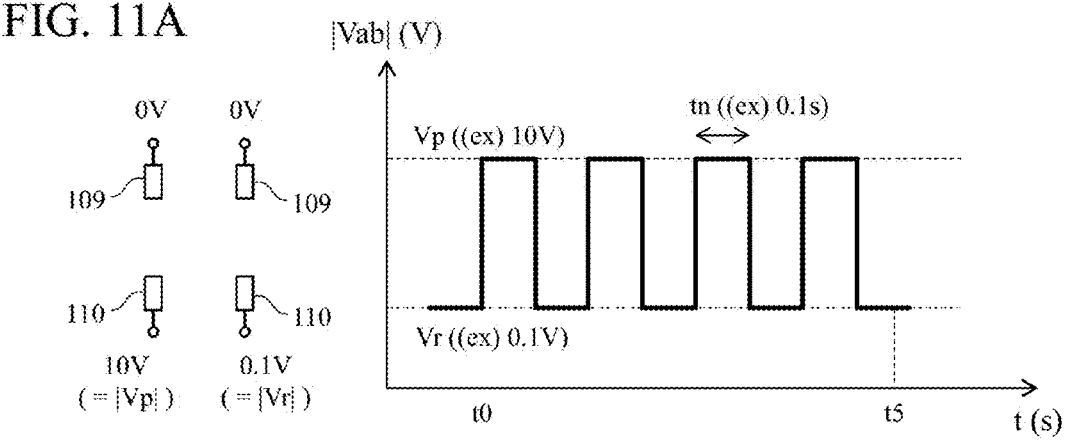
FIGS. 11A and 11B are a schematic view and a graph for describing a modification of the first embodiment.
Figure 11B:
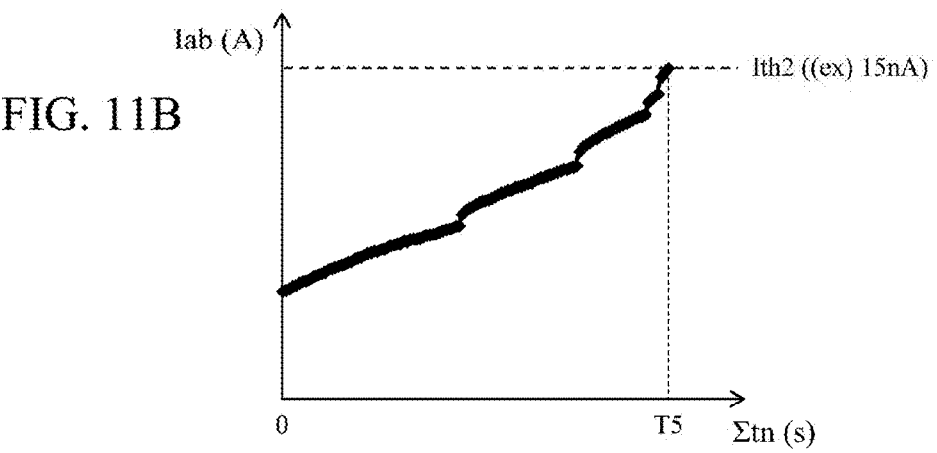

FIGS. 11A and 11B are a graph for describing a modification of the first embodiment. FIG. 11A is a schematic view and a graph illustrating an application voltage in a second step according to the modification of the first embodiment. In addition, FIG. 11B is a graph illustrating a change in current Iab in the second step.

This modification is the same as the first embodiment in terms that a single nanopore is formed in the membrane 113 by two steps of a first step and the second step. In addition, the voltage application in the first step is the same as that of the first embodiment (see FIGS. 8A and 8B).

In this modification, however, the application voltage in the second step is different from that of the above-described first embodiment. In this modification, as illustrated in FIG. 11A, a polarity of a pulse voltage in the second step is the same as a polarity of the application voltage in the first step (that is, the polarity of the application voltage illustrated in FIGS. 8A and 8B) (in the example of FIGS. 11A and 11B, Vp is output by applying 0 V to the electrode 109 and 10 V to the electrode 110).

That is, in the example of FIGS. 11A and 11B, the pulse width to of the pulse voltage in the second step is 0.1 s, a pulse voltage |Vp| is 10 V, and a voltage |Vr| between the pulse voltages is 0.1 V. This point is the same as the first embodiment. In this modification, however, the pulse voltage of 10 V (voltage of the same polarity as that in the first step) is applied by applying 0 V to the electrode 109 and applying 10 V to the electrode 110 at the time of applying the pulse voltage in the second step, which is the only difference from the first embodiment.

The horizontal axis of the graph of FIG. 11B indicates an integrated time (Σtn) of an application time of the pulse voltage having the pulse width tn, which is similar to FIG. 9B. Similarly, the vertical axis of the graph indicates a value of the current Iab between the electrodes 109 to 110 measured when Vr=0.1 V is applied to determine the degree of breakdown of the thin film portion. In the example of FIG. 11B, the current Iab becomes equal to or larger than the threshold current Ith2=15 nA when the integrated time (Σtn) of the application time of the pulse voltage reaches T5, and as a result, the second step ends. It has been found by experiments of the inventors that the integrated time T5 reaches the integrated time T4 approximately several times in the case of FIG. 9B. According to the experiments of the present inventors, it has been found that the integrated time T4 is about 2 seconds, whereas the integrated time T5 is about 10 to 12 seconds. In addition, it has also been found that a variation in size of the formed holes is large in the case of using the modification of the first embodiment (that is, the polarity of the pulse voltage in the second step is the same as the polarity of the application voltage in the first step) as compared with the case of using the above-described first embodiment (that is, the polarity of the pulse voltage in the second step is opposite to the polarity of the application voltage in the first step). Therefore, it is preferable that the polarity of the pulse voltage Vp in the second step be opposite to the polarity of the application voltage in the first step in view of the time required for nanopore formation and the variation in size of the formed nanopores. On the other hand, as an advantage of the modification of the first embodiment (that is, the polarity of the pulse voltage in the second step is the same as the polarity of the application voltage in the first step), all the voltages applied between the electrodes in the first step and the second step can be set to the same polarity, and thus, a power supply required for the voltage application between the electrodes may be either a positive power supply or a negative power supply. This facilitates design of a power supply circuit, and a size of the power supply circuit can be also reduced, so that there is an advantage that the measurement control unit 112 can be manufactured at lower cost.

Note that the membrane 113 having the thickness of 20 nm is used in the example described above, but the thickness of the membrane 113 is not limited thereto. For example, even when the thickness of the membrane 113 is different, a nanopore having a pore diameter of about 20 nm can be formed with substantially the same setting as the above setting. The present inventor has conducted a similar experiment with the membrane 113 having a thickness of 14 nm. For example, in the first step, 0 V was applied to the electrode 109, and 11 V was applied to the electrode 110, and the application was automatically stopped when the current Iab between the electrodes 109 to 110 reached the threshold current Ith1=1×10$^{-6}$ A. Then, in the second step, application of a pulse voltage (pulse width tn =0.1 s) by applying 9 V to the electrode 109 and 0 V to the electrode 110 and measurement of the current between the electrodes 109 and 110 by applying |Vr|=0.1 V by applying 0 V to the electrode 109 and 0.1 V to the electrode 110 were repeated, and the second step was ended when the current reached the threshold current Ith2=15 nA. As a result, it has been found that nanopores having a pore diameter of about 20 nm were formed stably on average.

In this manner, the method according to the present embodiment is advantageous for membranes having various thicknesses. The method according to the present embodiment is particularly advantageous for a membrane having a large thickness, but is also effective for a membrane having a small thickness (for example, 5 nm or less). That is, it has been found that the single nanopore can be more stably formed in one membrane by dividing a hole formation step into the first step and the second step as described above as in the present embodiment even for a membrane having a small thickness.

In addition, the material of the membrane 113 is SiN in the above-described example, but the material of the membrane 113 is not limited to SiN, and the hole forming method according to the present embodiment is also advantageous for other materials. Specific examples of the membrane 113 include, for example, SiN, $SiO_2$, $HfO_2$, $Al_2O_3$, $HfAlO_x$, $ZrAlO_x$, $Ta_2O_5$, SiC, SiCN, a carbon film, and a composite thereof.

In addition, the hole formation in the membrane used for DNA sequencing and other biological analysis device has been described as an example in the above description, but it is needless to say that the present embodiment can be applied to membranes in other fields in which nanopores having the same size need to be formed.

In addition, the voltage, the threshold current, the pulse width, and the like described in the above-described example are merely examples, and the present invention is not limited thereto. Meanwhile, it is desirable that the magnitude of the application voltage in the first step be between 0.1 V/nm and 2 V/nm when the application voltage is divided by the thickness of the membrane 113. When (application voltage/thickness of membrane 113) is less than 0.1 V/nm, the time required until the current Iab between the electrodes reaches the set threshold current Ith1 becomes extremely long, and as a result, the time required for the first step becomes extremely long. On the other hand, when (application voltage/thickness of membrane 113) is more than 2 V/nm, the time required until the current Iab between the electrodes reaches the set threshold current since the application of the voltage becomes extremely short, and thus, it is difficult to control the first step using a commercially available general measurement control unit.

In addition, the threshold current Ith1 used to stop the application voltage in the first step is set to $10^{-6}$ A in the above-described example, but this value is merely an example and is not limited thereto. The threshold current Ith1 only has to be set to such an extent that a thin film portion having a sufficiently smaller thickness than the original thickness of the membrane 113 is formed. However, it is preferable to set the threshold current Ith1 in the range of between 1 nA and 5 µA in view of the purpose of forming the single nanopore in one membrane. When the threshold current Ith1 is set to be larger than 5 µA, the probability that a plurality of holes having different sizes are generated in one membrane 113 as illustrated in the image of FIG. 7 increases. On the other hand, when the threshold current Ith1 is set to be smaller than 1 nA, it becomes difficult to form a clear thin film portion in the membrane 113 even if the first step is performed for a long time, and no hole is opened in the membrane 113 even after the second step in many cases.

The magnitude of the application voltage Vp in the second step is not limited to the above-described numeric value. However, the application voltage when being divided by the thickness of the membrane 113 (the thickness of the membrane 113 in a portion other than the thin film portion formed in the first step) is desirably set between 0.1 V/nm and 1.5 V/nm When (application voltage/membrane thickness) is smaller than 0.1 V/nm, the time required until the current Iab between the electrodes reaches the set threshold current Ith2 becomes extremely long, and as a result, the time required for the second step becomes extremely long. On the other hand, when (application voltage/membrane thickness) is larger than 1.5 V/nm, the probability that two or more holes are formed in the membrane 113 increases.

In addition, the pulse width tn of the pulse voltage in the second step is set to 0.1 s in the above-described example, but the pulse width tn is not limited thereto, and is set to an arbitrary value as long as the single nanopore can be formed in one membrane with high probability. However, it is preferable to set the pulse width tn between 1 µs and 10 s. If the pulse width tn is smaller than 1 µs, there is a high possibility that the voltage applied between the electrodes 109 and 110 is not sufficiently applied to the membrane 113. As a result, the time required until the completion of the second step becomes extremely long. On the other hand, when the voltage pulse width tn is larger than 10 s, there is a possibility that the current between the electrodes 109 and 110 measured by applying the low voltage (Vr) after the application of the pulse voltage significantly exceeds the preset threshold current Ith2. Then, there is a possibility that a hole much larger than a desired hole is formed.

In the case of applying the pulse voltage in the second step, it is desirable to set the threshold current Ith2 to be between twice and 100 times the current Iint flowing between the electrodes 109 and 110 when the voltage (Vr) is applied before the start of the application of the pulse voltage. When the threshold current Ith2 is smaller than twice the current Iint, the probability that the thin film portion formed in the first step is not broken and no hole is formed increases. On the other hand, if the threshold current Ith2 is larger than 100 times the current Iint, the time required until the completion of the second step becomes extremely long, and the probability that two or more holes are opened in the membrane 113 increases.

In addition, the examples of forming nanopores having a diameter of about 20 to 30 nm have been illustrated in the experimental examples described above, it has been also found that the diameter of the formed nanopore can be controlled depending on the settings of Ith1 and Ith2. That is, it is sufficient to set the values of Ith1 and Ith2 to be small when it is desired to create a nanopore having a smaller diameter, and it is sufficient to set the values of Ith1 and Ith2 to be large when it is desired to create a nanopore having a larger diameter.

In addition, it is desirable to set the magnitude of the application voltage |V1| in the first step and the magnitude of the pulse voltage |Vp| in the second step such that |VP|<|V1| is satisfied as described above. The reason thereof is to prevent a nanopore from being formed in a region other than the thin film portion formed in the first step (that is, to prevent formation of a plurality of nanopores). When |vp|=|V1| is satisfied, it is necessary to adjust the application time width to of the pulse voltage to be sufficiently short such that the nanopore is opened only in the thin film portion formed in the first step.

Second Embodiment

A hole forming apparatus and a hole forming method according to a second embodiment will be described with reference to FIGS. 12A, 12B, 13A and 13B. An external configuration of the hole forming apparatus according to the second embodiment is substantially the same as that of the first embodiment (FIG. 1), and thus the redundant description thereof will be omitted. However, voltage control in the hole forming method, specifically, the control performed by the measurement control unit 112 is different from that of the first embodiment.

Figure 12A:
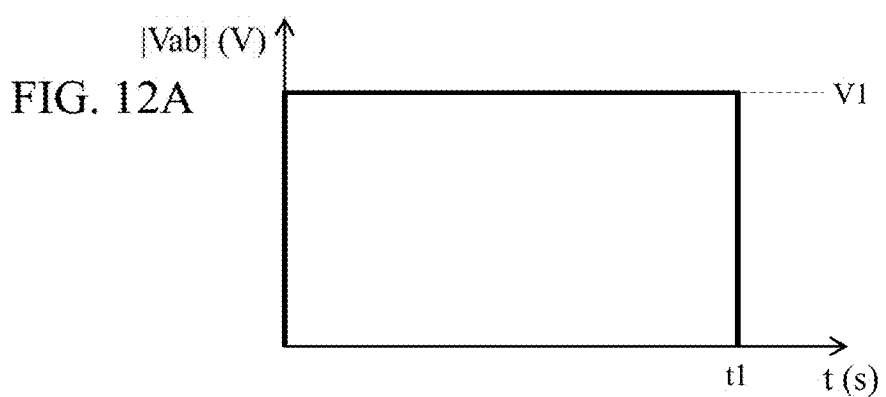
FIGS. 12A and 12B are a graph for describing a hole forming method according to a second embodiment.
Figure 12B:
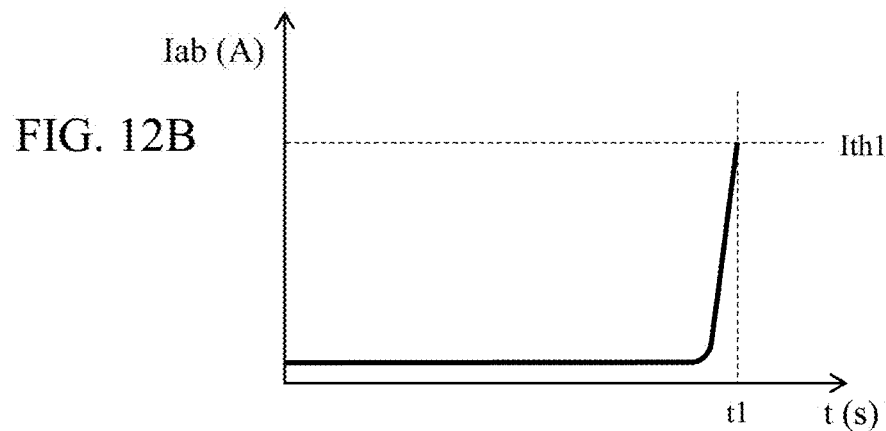

The hole forming method according to the second embodiment is the same as that of the first embodiment in terms that voltage application divided into a first step and a second step is performed. In addition, in the voltage application in the first step, the voltage Vab applied between the electrodes 109 and 110 is set to the voltage V1, and the application of the voltage V1 between the electrodes 109 and 110 is stopped when the current Iab between the electrodes 109 and 110 reaches the threshold current Ith1, thereby forming a thin film portion in a part of the membrane as illustrated in FIGS. 12A and 12B. This is the same as that of the first embodiment.

Figure 13A:
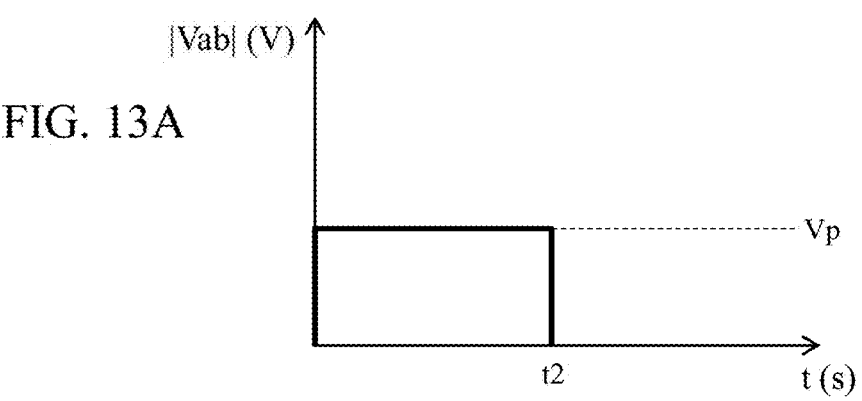
FIGS. 13A and 13B are a graph for describing the hole forming method according to the second embodiment.
Figure 13B:
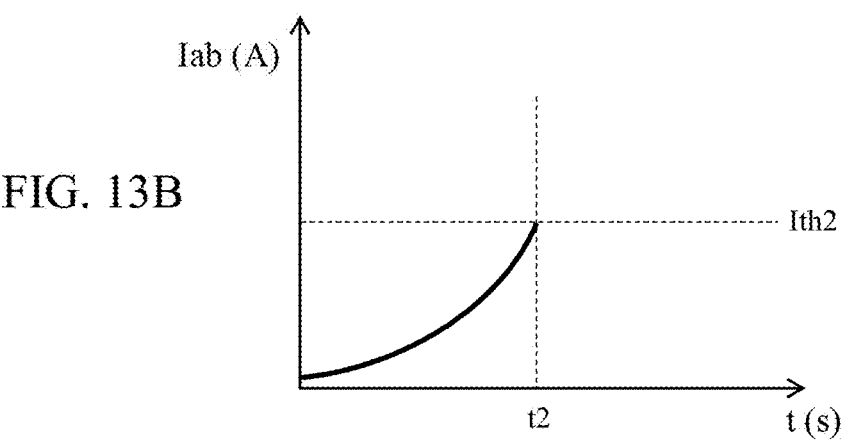

As illustrated in FIGS. 13A and 13B, a voltage application method in the second step is different from that of the first embodiment. In the second step according to the second embodiment, the constant voltage Vab=Vp is continuously applied between the electrodes 109 and 110 without using a pulse voltage as in the first embodiment. Note that |Vp|<|V1| is satisfied. Then, such application of the voltage Vab=Vp advances the breakdown of the thin film portion, and the application of the voltage Vab is stopped when the current Iab between the electrodes 109 and 110 reaches the threshold current Ith2 at time t2, for example. According to such a voltage application method, it is possible to form a single nanopore in one membrane as in the first embodiment. The values of the threshold current Ith2 and the voltage value V2 can be set to values different from those of the first embodiment. Note that the voltage Vp may have the opposite polarity of or the same polarity as the polarity of the voltage V1 in the first step. However, the time required to reach the threshold current Ith2 in the second step is shorter when the voltages Vp and V1 have opposite polarities (opposite directions) even in the second embodiment, which is similar to the case of the first embodiment. In addition, it has also been found that a variation in size of formed holes is smaller when the voltage Vp and the voltage V1 have opposite polarities (opposite directions). Therefore, it is preferable to use the opposite polarities in consideration of the time required for nanopore formation and the variation in size of the formed nanopores. On the other hand, it is sufficient to prepare either a positive power supply or a negative power supply as a power supply for applying the voltage to the electrodes 109 and 110 by setting the voltage Vp and the voltage V1 to have the same polarity as also described in the description of the first embodiment. This facilitates design of a power supply circuit, and a size of the power supply circuit can be also reduced, so that there is an advantage that the measurement control unit 112 can be manufactured at lower cost.

It is desirable to set the threshold current Ith2 set in the second step to be between twice and 100 times the current Iab measured at the stage where a transient current flowing between the electrodes 109 to 110 converges to some extent after a lapse of about 5 to 10 seconds since the start of the second step (after a lapse of about 5 to 10 seconds immediately after the start of the application of the voltage value Vp). When the threshold current Ith2 is set to a value smaller than the above range, the probability that the thin film portion formed in the membrane 113 in the first step cannot be broken and no hole is formed increases. In addition, when the threshold current Ith2 is set to a value larger than the above range, the time required until the completion of the second step becomes extremely long, and further, there is a high possibility that two or more holes are opened in the membrane 113.

Third Embodiment

A hole forming apparatus and a hole forming method according to a third embodiment will be described with reference to FIGS. 14A and 14B. An external configuration of the hole forming apparatus according to the third embodiment is substantially the same as that of the first embodiment (FIG. 1), and thus the redundant description thereof will be omitted. However, voltage control in the hole forming method, specifically, the control performed by the measurement control unit 112 is different from that of the first embodiment.

In the hole forming method according to the third embodiment, voltage application in a first step is different from those of the above-described embodiments. The voltage application in the second step may be the same as that in any of the above-described embodiments.

In the first step according to the third embodiment, the voltage Vab is set to a start value Vst smaller than a target value Vtg, and thereafter, the voltage Vab is gradually increased with time. For example, as illustrated in FIG. 14A, the voltage Vab is repeatedly increased in a stepwise manner at a predetermined step-up width Vs after maintaining a certain voltage for a certain time ts, and finally increased to the target value Vtg. The measurement control unit 112 monitors whether or not the current Iab between the electrodes 109 and 110 has reached the threshold current Ith1 while increasing the voltage Vab in this manner, and stops the application of the voltage Vab when the current Iab reaches the threshold current Ith1 at time t1' as illustrated in FIG. 14B.

An advantage of the third embodiment is that the time required until the completion of the first step can be shortened, for example, by shortening the time is in FIG. 14A or by increasing the step-up width Vs. In addition, in the third embodiment, the application voltage Vab is gradually increased with time in the first step. Accordingly, the third embodiment is advantageous when it is not clear how much voltage should be applied, and for how many seconds the voltage should be applied to cause dielectric breakdown on the membrane 113 as a processing target. A method for increasing the voltage Vab is not limited to the above-described stepwise manner, but the voltage Vab can be increased continuously and linearly.

Note that, when the first step as in the third embodiment is performed, the magnitude Vp of the voltage applied in the subsequent second step is set to be a voltage having an absolute value smaller than an absolute value of a voltage value Vfin applied when the current Iab between the electrodes 109 and 110 reaches the threshold current Ith1 in the first step.

Fourth Embodiment

A hole forming apparatus and a hole forming method according to a fourth embodiment will be described with reference to FIG. 15 to FIGS. 19A and 19B. An external configuration of the hole forming apparatus according to the fourth embodiment is substantially the same as that of the first embodiment (FIG. 1), and thus the redundant description thereof will be omitted. However, voltage control in the hole forming method, specifically, the control performed by the measurement control unit 112 is different from that of the first embodiment.

In the hole forming method according to the fourth embodiment, voltage application in a first step is different from those of the above-described embodiments. The voltage application in the second step may be the same as that in any of the above-described embodiments.

In the first step in the fourth embodiment, the voltage Vab can have an AC waveform (sine waveform) as illustrated in FIG. 15. That is, a direction (polarity) of the voltage Vab changes periodically in the fourth embodiment.

Figure 16:
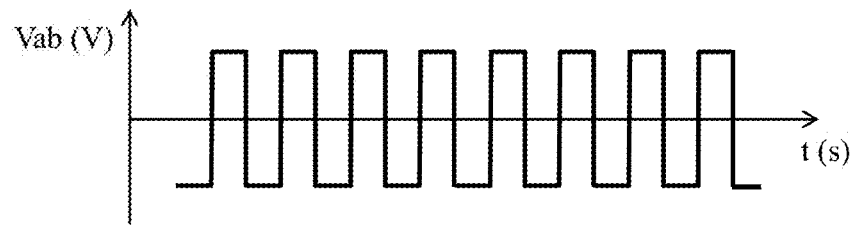
FIG. 16 is a graph for describing the hole forming method according to the fourth embodiment.
Figure 17:
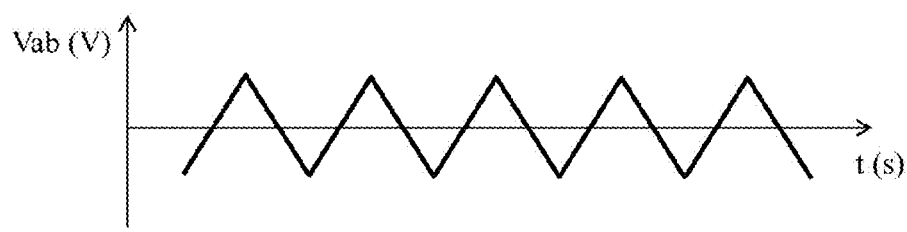
FIG. 17 is a graph for describing the hole forming method according to the fourth embodiment.
Figure 18:
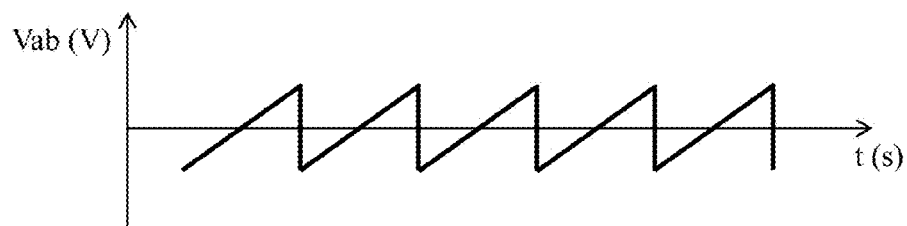
FIG. 18 is a graph for describing the hole forming method according to the fourth embodiment.

In addition, the waveform is not limited to the sine wave, and may be a waveform, such as a rectangular wave, a triangular wave, and a sawtooth wave as illustrated in FIGS. 16 to 18, for example, whose voltage value and/or polarity changes periodically over time. Note that these waveforms may be superimposed on a DC voltage.

When an AC voltage is used as an application voltage in the first step, the current flowing between the electrodes 109 and 110 also becomes AC. Therefore, the threshold current Ith1 used for determination on whether to end the first step is preferably defined by a value of an effective value of the current Iab between the electrodes 109 and 110. That is, the first step is set to end when the effective value of the current Iab between the electrodes 109 and 110 reaches a certain threshold, thereby forming a thin film portion in the membrane 113.

In addition, in the case of using the AC voltage for the voltage application in the first step, a difference between a phase of the applied AC voltage Vab and a phase of the detected current Iab increases when a predetermined thin film portion is formed in the membrane 113. Therefore, it is also possible to end the application of the AC voltage Vab when the phase difference reaches a certain threshold. Alternatively, it is also possible to determine whether to end the first step using information on both the effective value of the current Iab and the phase difference.

In addition, the application voltage in the first step may be a voltage where an AC voltage and a DC voltage appear alternately.

When at least one component of the application voltage in the first step is set to the AC voltage as in the fourth embodiment, it is possible to improve the vertical symmetry of a shape of a nanopore formed in the membrane 113. For example, a case where upper and lower sides of the nanopore are symmetric corresponds to a shape illustrated in FIG. 19A, and a case where the nanopore is vertically asymmetric corresponds to a shape illustrated in FIG. 19B.

When the fourth embodiment is implemented, a side wall of the nanopore 114 formed in the membrane 113 can be formed at an angle closer to be perpendicular to the surface of the membrane 113 as illustrated in FIG. 19A.

When a side surface of the nanopore 114 has a shape that is perpendicular to the surface of the membrane 113 and is vertically symmetric, a detection target is less likely to clog the nanopore 114, and the detection accuracy of the target can be improved.

Fifth Embodiment

A hole forming apparatus and a hole forming method according to a fifth embodiment will be described with reference to FIGS. 20 and 21. An external configuration of the hole forming apparatus according to the fifth embodiment is substantially the same as that of the first embodiment (FIG. 1), and thus the redundant description thereof will be omitted. However, voltage control in the hole forming method, specifically, the control performed by the measurement control unit 112 is different from that of the first embodiment.

In the hole forming method according to the fifth embodiment, voltage application in a second step is different from those of the above-described embodiments. The voltage application in the first step may be the same as that in any of the above-described embodiments.

In the second step according to the fifth embodiment, an AC voltage at a certain time width (the maximum voltage=Vpc, the minimum voltage=−Vpc) and a DC voltage (the voltage magnitude Vr) whose absolute value is smaller than Vpc are repeatedly applied between the electrodes 109 and 110 to be alternate in time, and a current flowing between the electrodes 109 and 110 at the time of applying voltage Vr is measured to determine whether the current has exceeded a threshold current. When the current exceeds the threshold current, it is determined that a nanopore has been formed, and the second step ends. A value of Vpc is preferably set to a value smaller than the magnitude of a voltage applied between the electrodes 109 and 110 at the time of detecting the completion of formation of a thin film portion in the first step.

In addition, the application voltage in the second step according to the fifth embodiment may be a voltage (the maximum value=Vpc+Vx, the minimum value=−Vpc+Vx) obtained by superimposing an AC voltage having an amplitude Vpc and a DC voltage having a voltage value Vx on each other as illustrated in FIG. 21. In this case, an absolute value |Vpc+Vx| of the maximum value of the application voltage in the second step is desirably set to a value smaller than the voltage applied at the time of detecting the formation of the thin film portion in the first step. Note that AC waveforms illustrated in FIGS. 20 and 21 are sine waveforms, but may be other waveforms of a rectangular wave, a triangular wave, a sawtooth wave, and the like. When at least one component of the application voltage in the second step is set to the AC voltage as in the fifth embodiment, it is possible to improve the vertical symmetry of a shape of a nanopore formed in the membrane 113. For example, a case where upper and lower sides of the nanopore are targets corresponds to the shape illustrated in FIG. 19A. When a side surface of the nanopore 114 has a shape that is perpendicular to the surface of the membrane 113 and is vertically symmetric, a detection target is less likely to clog the nanopore 114, and the detection accuracy of the target can be improved.

Although some embodiments of the present invention have been described as above, these embodiments have been presented by way of example only, and are not intended to limit the scope of the invention. These novel embodiments can be implemented in other various modes, and various omissions, replacements, and changes can be made without departing from the gist of the invention. These embodiments and modifications thereof are included in the scope and gist of the invention, and are also included in the inventions described in the claims and their equivalents.

REFERENCE SIGNS LIST

100 Si substrate
101 SiN film
102 SiO$_2$ film
103 SiN film
104 O-ring
105, 106 chamber
107, 108 electrolyte
109, 110 electrode
111 wiring
112 measurement control unit
113 membrane
114 nanopore

The invention claimed is:

1. A hole forming method for forming a hole in a film, the hole forming method comprising:
a first step of applying a first voltage between a first electrode and a second electrode, installed so as to sandwich the film provided in an electrolyte, and stopping the application of the first voltage when a current flowing between the first electrode and the second electrode reaches a first threshold current so as to form a thin film portion in a part of the film; and
a second step of applying a second voltage between the first electrode and the second electrode after the first step so as to form a nanopore in the thin film portion.

2. The hole forming method according to claim 1, wherein in the second step, the application of the second voltage is stopped when the current flowing between the first electrode and the second electrode reaches a second threshold current.

3. The hole forming method according to claim 1, wherein the second voltage has an absolute value equal to or smaller than an absolute value of the first voltage.

4. The hole forming method according to claim 1, wherein the second voltage has an opposite polarity of a polarity of the first voltage.

5. The hole forming method according to claim 1, wherein the first voltage is gradually increased from a first value toward a second value larger than the first value.

6. The hole forming method according to claim 1, wherein the first voltage includes a component of an AC voltage.

7. The hole forming method according to claim 1, wherein the second voltage includes a component of an AC voltage.

8. The hole forming method according to claim 1, wherein in the second step, a third voltage is applied between the first electrode and the second electrode after applying the second voltage to measure a current flowing between the first electrode and the second electrode, and the application of the second voltage and the measurement of the current during the application of the third voltage are repeated until the current reaches or exceeds a third threshold current.

9. The hole forming method according to claim 8, wherein the third voltage is lower than the second voltage.

10. The hole forming method according to claim 8, wherein a width of one application time of the second voltage is between 1 μs and 10 s.

11. The hole forming method according to claim 8, wherein the third voltage is between 0.01 V and 1 V.

12. A hole forming apparatus comprising:
a first electrode and a second electrode arranged so as to sandwich a film provided in an electrolyte; and
a control unit including a storage unit that stores a first value of a first threshold current that will form a thin film portion in a part of the film without penetrating the film, and a second value of a second threshold current that will form a nanopore on the thin film portion;
wherein the control unit is configured to perform the following functions:
applying a first voltage between the first electrode and the second electrode; and
automatically stopping the application of the first voltage when the current flowing between the first electrode and the second electrode reaches the first threshold current thereby forming the thin film portion in a part of the film without penetrating the film; and
after automatically stopping the application of the first voltage, applying a second voltage between the first electrode and the second electrode thereby forming a nanopore in the thin film portion.

13. The hole forming apparatus according to claim 12, wherein the control unit is further configured to perform a function of:
automatically stopping the application of the second voltage when the current flowing between the first electrode and the second electrode reaches the second threshold current thereby forming the nanopore in the thin film portion.

14. The hole forming apparatus according to claim 12, wherein the second voltage has an absolute value smaller than an absolute value of the first voltage.

15. The hole forming apparatus according to claim 12, wherein the second voltage has an opposite polarity of a polarity of the first voltage.

16. The hole forming apparatus according to claim 12, wherein
the first voltage includes a component of an AC voltage.

17. The hole forming apparatus according to claim 12, wherein
the second voltage includes a component of an AC voltage.

18. The hole forming apparatus according to claim 12, wherein in the second step, a third voltage is applied between the first electrode and the second electrode after applying the second voltage to measure a current flowing between the first electrode and the second electrode, and the application of the second voltage and the measurement of the current during the application of the third voltage are repeated until the current reaches or exceeds a third threshold current.

19. A hole forming method for forming a single hole in a film, the hole forming method comprising:
storing a first value of a first threshold current that will form a thin film portion of the film without penetrating the film, and a second value of a second threshold current that will form the single hole in the thin film portion, thereby forming the single hole in the film;
performing a first step of applying a first voltage between a first electrode and a second electrode, installed so as to sandwich the film provided in an electrolyte, and stopping the application of the first voltage when a current flowing between the first electrode and the second electrode reaches the first threshold current thereby ending the first step without penetrating the film; and
performing a second step of applying a second voltage having an opposite polarity of a polarity of the first voltage between the first electrode and the second electrode after performing the first step.

20. The hole forming method according to claim 19, wherein
in performing the second step, the application of the second voltage is stopped when the current flowing between the first electrode and the second electrode reaches the second threshold current.

21. The hole forming method according to claim 19, wherein the second voltage has an absolute value equal to or smaller than an absolute value of the first voltage.

22. The hole forming method according to claim 19, wherein in the second step, a third voltage is applied between the first electrode and the second electrode after applying the second voltage to measure a current flowing between the first electrode and the second electrode, and the application of the second voltage and the measurement of the current during the application of the third voltage are repeated until the current reaches or exceeds a third threshold current.

23. The hole forming method according to claim 22, wherein the third voltage is lower than the second voltage.

* * * * *